(12) United States Patent
Deaton et al.

(10) Patent No.: US 6,565,583 B1
(45) Date of Patent: May 20, 2003

(54) ENDARTERECTOMY APPARATUS AND METHOD

(75) Inventors: David H. Deaton, Crownsville, MD (US); Steve G. Baker, Sunnyvale, CA (US)

(73) Assignee: Acumen Vascular, Inc., Sunnyvale, CA (US)

( * ) Notice: Subject to any disclaimer, the term of this patent is extended or adjusted under 35 U.S.C. 154(b) by 0 days.

(21) Appl. No.: 09/611,837

(22) Filed: Jul. 7, 2000

Related U.S. Application Data
(60) Provisional application No. 60/142,992, filed on Jul. 8, 1999.

(51) Int. Cl.[7] .............................. A61B 17/22; A61D 1/02
(52) U.S. Cl. ........................ 606/159; 606/127; 606/167
(58) Field of Search ........................... 606/1, 159, 166, 606/167, 170, 171, 190, 191; 30/280, 316; 15/104.05, 104.16, 104.17; 600/207

(56) References Cited

U.S. PATENT DOCUMENTS

| | | | | |
|---|---|---|---|---|
| 88,405 A | * | 3/1869 | Morse et al. ............. | 15/140.16 |
| 4,315,511 A | * | 2/1982 | Chin ........................... | 606/159 |
| 5,549,625 A | * | 8/1996 | Bircoll ........................ | 606/192 |
| 5,665,098 A | * | 9/1997 | Kelly et al. ................. | 606/159 |
| 5,820,629 A | * | 10/1998 | Cox ............................ | 606/159 |
| 6,036,713 A | * | 3/2000 | Kieturakis .................. | 606/190 |

\* cited by examiner

*Primary Examiner*—Amy Vanatta
*Assistant Examiner*—Robert H. Muromoto, Jr.
(74) *Attorney, Agent, or Firm*—James J. Leary; Carol D. Titus

(57) ABSTRACT

Improved apparatus and methods are described for performing endarterectomy remotely via intraluminal techniques. A flexible blade dissector has a curved, diamond-shaped flexible dissecting blade mounted on a catheter shaft. The distal edge of the flexible dissecting blade is configured to form a dissecting edge for separating an atheromatous plaque from the medial layer of an artery wall. The flexible blade dissector may incorporate a steering mechanism to direct the flexible dissecting blade along a preferred path within the arterial wall. The endarterectomy method is performed by making an incision into an artery wall and initiating a plane of separation between an atherosclerotic plaque and the medial layer of the artery wall, inserting the flexible blade dissector into the plane of separation and advancing the flexible dissecting blade to longitudinally extend the plane of separation. Optionally, a second flexible blade dissector with a wider dissecting blade may be inserted coaxially over the catheter shaft of the first flexible blade dissector and advanced to laterally expand the plane of separation. Once the plaque has been freed from the entire inner circumference of the arterial lumen, the plane of separation is terminated on the distal and proximal ends, and the plaque is removed from the arterial lumen.

24 Claims, 14 Drawing Sheets

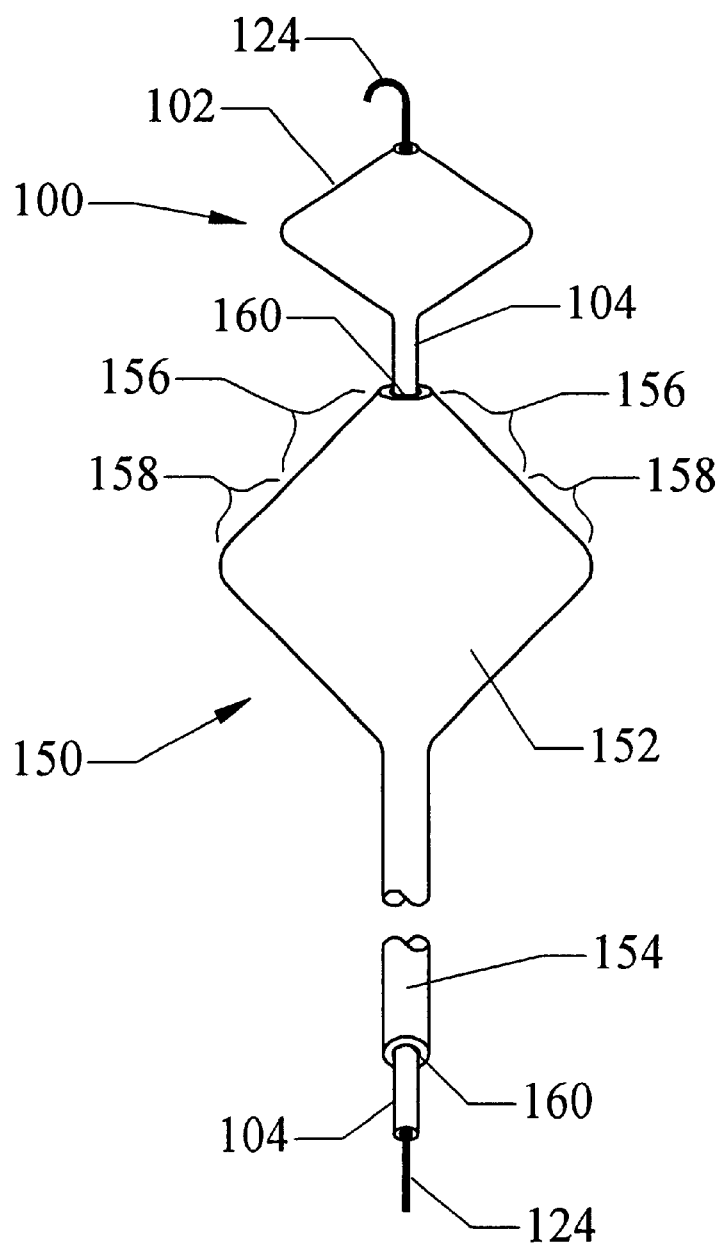

ENDARTERECTOMY APPARATUS AND METHOD

RELATIONSHIP TO OTHER APPLICATIONS

This application claims the benefit of U.S. provisional patent application No. 60/142,992, filed Jul. 8, 1999, the entire disclosure of which is hereby incorporated by reference.

FIELD OF THE INVENTION

The present invention relates to surgical apparatus and methods. In particular, it relates to apparatus and methods for treatment of blockages in body passages, particularly for removal of atherosclerotic plaques from arteries via endarterectomy.

BACKGROUND OF THE INVENTION

Atherosclerosis is a progressive disease of the cardiovascular system characterized by a buildup of plaques within a patient's arteries, resulting in a stenosis (narrowing) or occlusion (blockage) of the arterial lumen. Atherosclerotic plaques are generally deposits of cholesterol and lipids within the intimal layer of the arteries, which may also become calcified over time. When the arterial lumen becomes too narrow, it can cause ischemia in the tissue and organs downstream of the blockage, resulting in pain (angina or claudication), dysfunction, necrosis and even death, depending on what organ systems are involved.

One of the common treatments for atherosclerosis is arterial bypass grafting, wherein an artificial or biological conduit or bypass graft is used to reroute blood flow around the blockage. This is a complex surgical procedure, sometimes involving considerable morbidity and a risk of eventual occlusion of the bypass graft as the underlying disease progresses. Other treatments include dilatation or angioplasty, in which a tapered dilator or a balloon catheter is used to push the plaque aside to open the arterial lumen, and atherectomy, which involves cutting and removal or comminution of the plaque material. Stenting is an adjunct to angioplasty and atherectomy in which a vascular endoprosthesis (a stent) is implanted in the artery to maintain an open lumen after dilating or debulking the lesion. These approaches are most effective for discrete, focal lesions and are less effective for long lesions and diffuse atherosclerotic disease. Clinical data also indicate that there is a significant percentage of restenosis after both angioplasty and atherectomy, even with stenting. Furthermore, angioplasty, atherectomy and stents are ineffective in arteries with total occlusions. However, because angioplasty and atherectomy can be performed using minimally invasive catheter techniques, these approaches are sometimes favored for treating lesions that are difficult to access surgically, for example in coronary artery disease.

For atherosclerotic lesions in arteries that are surgically accessible, particularly long or diffuse lesions, endarterectomy is considered to be a more definitive treatment than angioplasty or atherectomy and, with advanced techniques, offers lower morbidity than surgical bypass. Endarterectomy involves surgically opening the artery, removing plaque from the interior of the artery and surgically closing the artery. To remove plaque, a plane of separation is established between the plaque and the medial layer of the artery. The plaque is dissected away from the media along the plane of separation and removed, along with the endothelial layer of the artery. If the plaque is long and extends beyond the portion of the artery to be treated, the plane of separation is smoothly terminated on its proximal and distal ends to prevent further dissection of the arterial wall. Endarterectomy has the advantage that it preserves the original arterial conduit, maintaining the original flow geometry and topology and offering a hemocompatible arterial lining with proven long-term patency. Endarterectomy actually removes the plaque rather than simply pushing it aside or routing blood flow around it. In addition, endarterectomy can also be used to effectively treat totally occluded arteries.

As an adjunct, a stent or stent graft may be implanted to re-line the vessel after endarterectomy. Alternatively or in addition, stents may be used in the transition zones at the ends of the treated portion of the artery to prevent further dissection of the arterial wall. The stent or stent graft will prevent abrupt reclosure and may reduce the occurrence of restenosis in the long term. Other adjunctive treatments may be used to reduce the chance of intimal hyperplasia or long term restenosis. These treatments include radiation therapy (e.g. brachytherapy), therapeutic ultrasound, local or systemic drugs and gene therapy.

Standard open endarterectomy has a disadvantage in that a long incision is required to expose and open the entire length of the arterial section to be treated. In order to reduce the size of the incision needed, and the concomitant morbidity involved, methods have been devised for performing endarterectomy less invasively. These methods generally involve making a series of small incisions at intervals along the length of the artery and using elongated instruments to separate and remove the plaques from the arterial lumen between the incisions, while keeping the arteries relatively intact. Examples of instruments for facilitating less invasive endarterectomy can be found in U.S. Pat. No. 4,290,427 to Albert K. Chin and Thomas J. Fogarty and in U.S. Pat. No. 5,843,102 to Menno Kalmann and Franciscus Laurens Moll, which are hereby incorporated in their entirety. Less invasive or remote endarterectomy has the advantages of standard endarterectomy and the additional advantages that it produces less trauma and morbidity than either standard endarterectomy or bypass surgery and, with the appropriate techniques, can entirely avoid the difficulty of end-to-side or end-to-end anastomoses. Although less invasive endarterectomy has a great many advantages, the current instruments and methods have limitations in terms of the length of the artery that can be treated through a single incision. They are also limited in the amount of variation allowable in the arterial wall that can be treated. Variations in the arterial wall that can interfere with treatment can be caused by tortuosity of the arteries and by changes in diameter of the artery over its length, as well as other factors. These limitations are closely related, since the longer the section of the artery to be treated, the more likely it is to have such variations in the arterial wall.

While the prior endarterectomy apparatus and methods represent a significant step forward in the treatment of atherosclerosis, continued research has been directed toward further improvements in the technology for performing endarterectomy. In particular, research has been directed toward devising instruments and methods that facilitate performing endarterectomy over longer lengths of artery, through fewer and smaller incisions and, ideally, to allow dissection, termination and removal of atherosclerotic plaques over long lengths of artery through a single incision. In furtherance of this goal, this research has also been directed toward devising apparatus and methods that will facilitate effective endarterectomy despite variations in the arterial wall due to tortuosity or diameter changes.

SUMMARY OF THE INVENTION

In keeping with the foregoing discussion, the present invention takes the form of improved apparatus and methods for performing endarterectomy remotely via intraluminal techniques. The endarterectomy apparatus of the present invention takes the form of a flexible blade dissector having a flexible dissecting blade mounted at the distal end of an elongated catheter shaft. In a preferred embodiment, the flexible dissecting blade is approximately diamond shaped, having approximately triangular shaped lateral wings arranged symmetrically on the left and right side of the catheter shaft. The distal edge of the flexible dissecting blade is configured as a dissecting edge capable of initiating and extending a plane of dissection between an atheromatous plaque and the medial layer of the artery without cutting into either the plaque or the tissue of the medial layer. The distal edge of the flexible dissecting blade may be sharpened to form a sharp dissecting edge or, alternatively, it may be rounded to form a blunt dissecting edge. The flexible dissecting blade is constructed to have differential stiffness such that the lateral wings will readily bend around a central longitudinal axis, but will resist bending perpendicular to this axis. Stiffeners or other structures may be incorporated into the flexible dissecting blade to enhance the differential stiffness. Preferably, the flexible dissecting blade is made with an initial curve, which helps it to conform to the curvature of the arterial wall. The flexible blade dissector may incorporate a steering mechanism to direct the flexible dissecting blade along a preferred path within the arterial wall.

In one preferred embodiment, the apparatus includes a first flexible blade dissector and a second flexible blade dissector that slides coaxially over the catheter shaft of the first flexible blade dissector. The flexible dissecting blade of the second device is made wider than the dissecting blade of the first device in order to expand the plane of dissection laterally within the arterial wall.

The endarterectomy method of the present invention is practiced by making an incision into an artery wall and initiating a plane of separation between an atherosclerotic plaque and the medial layer of the artery wall, inserting the flexible blade dissector into the plane of separation and advancing the flexible dissecting blade to longitudinally extend the plane of separation. Optionally, a second flexible blade dissector may be inserted into the plane of separation coaxially over the catheter shaft of the first device and advanced to laterally expand the plane of separation. Once the plaque has been freed from the entire inner circumference of the arterial lumen, the plane of separation is terminated on the distal and proximal ends if necessary, and the plaque is removed from the arterial lumen, using known techniques.

BRIEF DESCRIPTION OF THE DRAWINGS

FIG. 1 shows a front view of the flexible blade dissector, FIG. 2 shows a distal end view and FIG. 3 shows a back view of the flexible blade dissector.

FIGS. 5 and 6 illustrate a coaxial system of flexible blade dissectors for performing remote endarterectomy via intraluminal techniques.

FIG. 7 is a front view, FIG. 8 is a distal end view and FIG. 9 is a side view of a distal portion of the flexible blade dissector.

FIG. 10 is a front view and FIG. 11 is a distal end view of a distal portion of the flexible blade dissector.

FIG. 12 is a front view and FIG. 13 is a distal end view of a distal portion of the flexible blade dissector.

FIG. 14 is a front view, FIG. 15 is a distal end view, FIG. 16 is a side view and FIG. 17 is a perspective view of a distal portion of the flexible blade dissector.

DETAILED DESCRIPTION OF THE INVENTION

Figure 2:
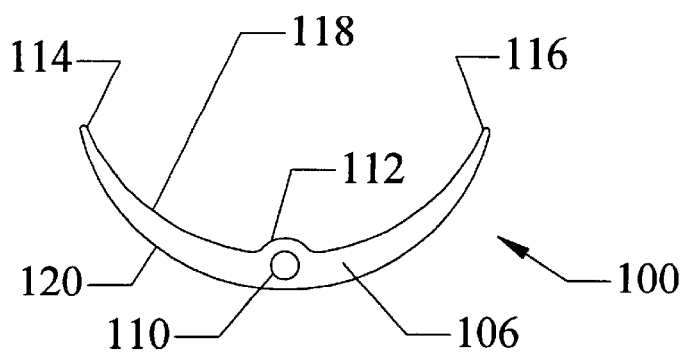
FIGS. 1, 2 and 3 illustrate a first embodiment of a flexible blade dissector for performing remote endarterectomy via intraluminal techniques.
Figure 1:
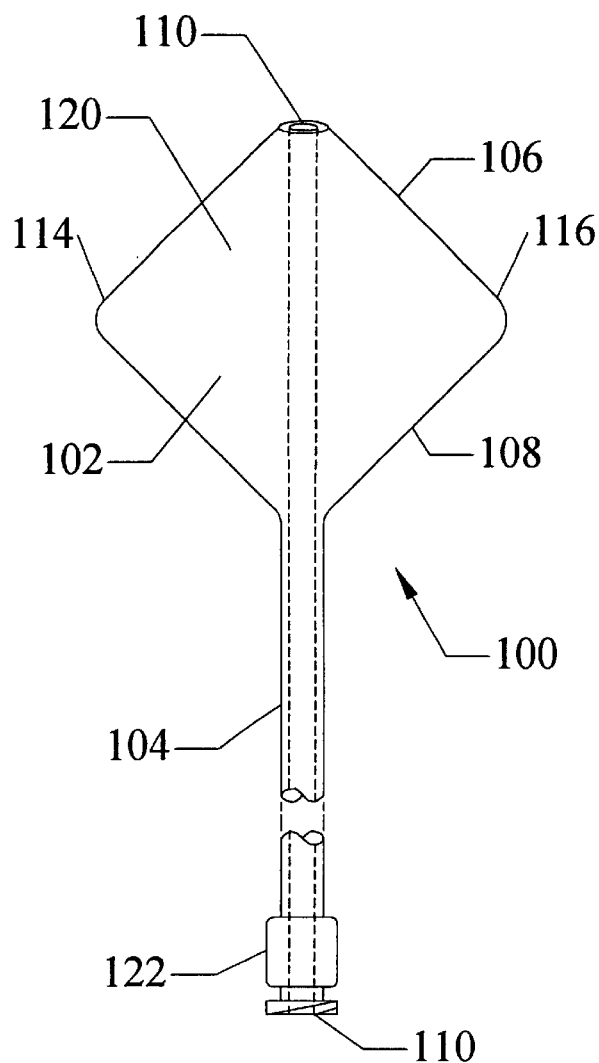
Figure 3:
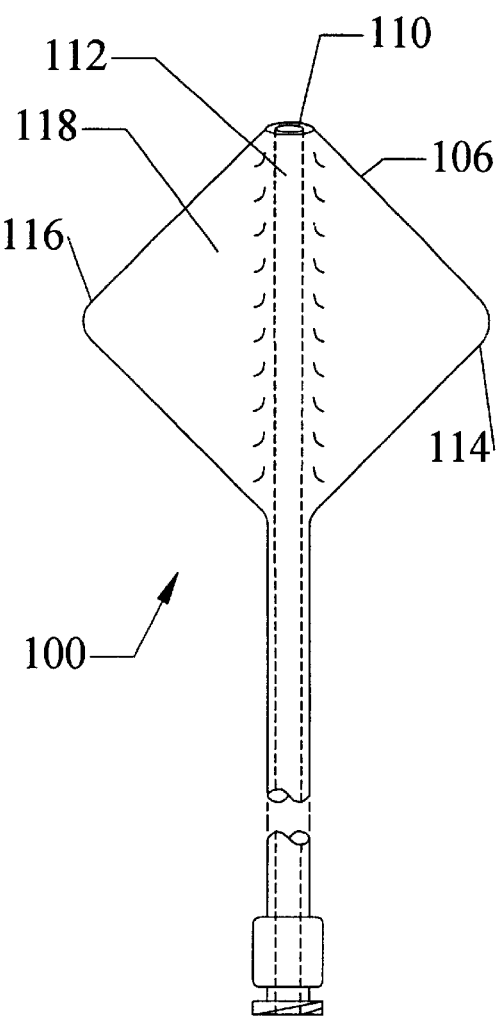

In keeping with the foregoing discussion, the present invention takes the form of improved apparatus and methods for performing endarterectomy remotely via intraluminal techniques. FIGS. 1, 2 and 3 illustrate a first embodiment of a flexible blade dissector 100 for performing remote endarterectomy via intraluminal techniques. FIG. 1 shows a front view of the flexible blade dissector 100, FIG. 2 shows a distal end view and FIG. 3 shows a back view of the flexible blade dissector 100. The flexible blade dissector 100 has a flexible dissecting blade 102 mounted at the distal end of an elongated catheter shaft 104. The flexible dissecting blade 102 has a distal edge 106 and a proximal edge 108. The distal edge 106 is configured as a dissecting edge capable of initiating and extending a plane of dissection between an atheromatous plaque and the underlying media without cutting into either the plaque or the tissue of the medial layer. In one preferred embodiment, the distal edge 106 of the flexible dissecting blade 102 is sharpened to form a sharp dissecting edge for initiating and extending the plane of dissection. In another preferred embodiment, the distal edge 106 of the flexible dissecting blade 102 is rounded to form a blunt dissecting edge for initiating and extending the plane of dissection by blunt dissection. The proximal edge 108 of the flexible blade dissector 100 maybe rounded and blunt.

Preferably, the elongated catheter shaft 104 is tubular in construction, having a guidewire lumen 110 that extends through the catheter shaft 104 and through the flexible blade dissector 100 to the distal edge 106. The guidewire lumen 110 is sized to provide a sliding fit over a guidewire, for example a standard 0.032, 0.035 or 0.038 inch diameter guidewire, a steerable guidewire or a specialized guidewire. Alternatively, the lumen 110 may be used for insertion of other instruments, such as an endoscope, a cutter, a snare, a grasper or other tools. The catheter shaft 104 is constructed to have sufficient column strength to advance the flexible blade dissector 100 along the plane of separation as the distal edge 106 dissects the plaque away from the media, while also having sufficient flexibility to follow the tortuosity of the arterial path. The catheter shaft 104, in this and each of the embodiments described herein, may be constructed of an extruded polymer or elastomer tube, a flexible metal tube or a composite construction, such as a braided wire reinforced polymer tube. The proximal end of the catheter shaft 104 is equipped with a fitting 122, such as a standard luer lock connector. If desired, the proximal end of the catheter shaft 104 may also be equipped with a hand grip or the like for improved handling and ergonomics. The length of the catheter shaft 104 is preferably between approximately 10 and 150 cm, more preferably from approximately 30 to 60 cm. The diameter of the catheter shaft 104 is preferably from approximately 1.5 to 3 mm.

The flexible dissecting blade 102 is generally spatulate in shape and flexible to conform to the inner curvature of the arterial wall. In one particularly preferred embodiment, the flexible dissecting blade 102 is approximately diamond shaped, having approximately triangular shaped lateral wings 114, 116 arranged symmetrically on the left and right side of the catheter shaft 104. The thickness of the lateral wings 114, 116 tapers down laterally away from a central ridge 112 located where the guidewire lumen 110 passes through the flexible dissecting blade 102, as shown in the distal end view of FIG. 2. The central ridge 112 of the flexible dissecting blade 102 is somewhat stiffer than the lateral wings 114, 116. This differential stiffness is further enhanced by the presence of a guidewire within the guidewire lumen 110. The differential stiffness of the flexible dissecting blade 102 may be further enhanced using any of the constructions described below in connection with FIGS. 7–12. The differential stiffness gives the flexible dissecting blade 102 a preferential bending geometry so that the lateral wings 114, 116 will readily bend around a central axis defined by the guidewire lumen 110 and the central ridge 112, but the flexible dissecting blade 102 resists bending perpendicular to this axis. In order to encourage the preferential bending geometry, the flexible dissecting blade 102 may be given an initial curve, as shown. In this case, the central ridge 112 is preferably placed on the concave side 118 of the curve so that the convex side 120 of the flexible dissecting blade 102 will be smooth. The width of the flexible dissecting blade 102 is preferably from approximately 25% to 125% of the vessel circumference, more preferably from approximately 33% to 100% of the vessel circumference. The flexible blade dissector 100 is typically intended to be used in arteries with a circumference from approximately 12 to 45 mm, although the device could be scaled larger or smaller for use in other vessels.

The flexible dissecting blade 102, in this and each of the embodiments described herein, is preferably made of a flexible polymer or elastomer. Suitable materials include, but are not limited to, polyethylene, polypropylene, polyolefins, polyvinylchloride, polyamides (nylons), polyurethanes, silicones, and copolymers, alloys and reinforced composites thereof. In addition, the flexible dissecting blade 102 may be coated with a low friction or lubricious coating.

Additionally, the flexible blade dissector 100 may include a steering mechanism, such as those described below in connection with FIGS. 19–43, to control the direction of the flexible blade dissector 100 as it dissects a plaque from the wall of the artery.

Figure 4A:
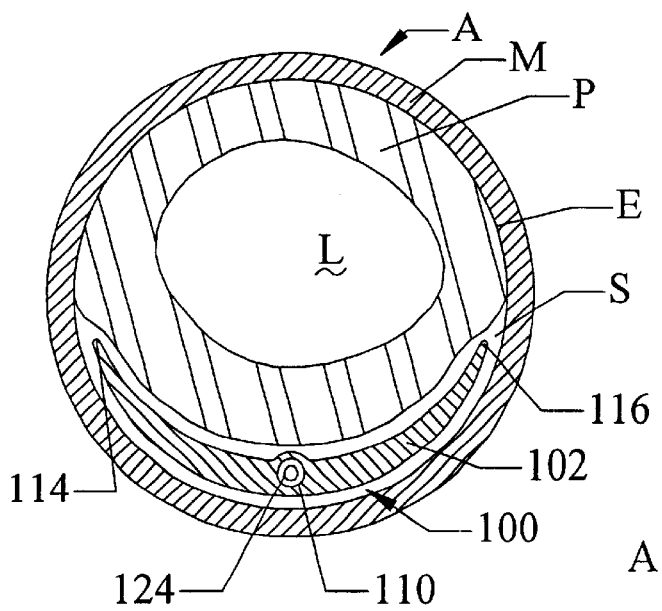
FIGS. 4A, 4B and 4C show the flexible blade dissector of FIGS. 1 and 2 in use for treating an artery using remote endarterectomy techniques.
Figure 4B:
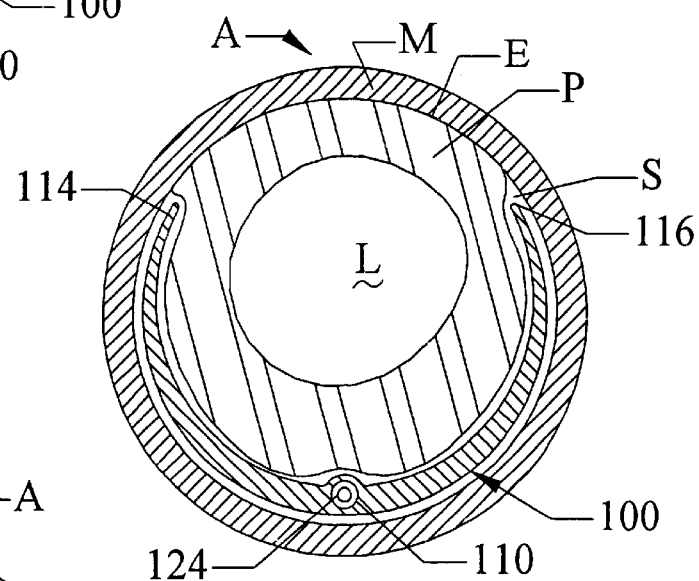
Figure 4C:
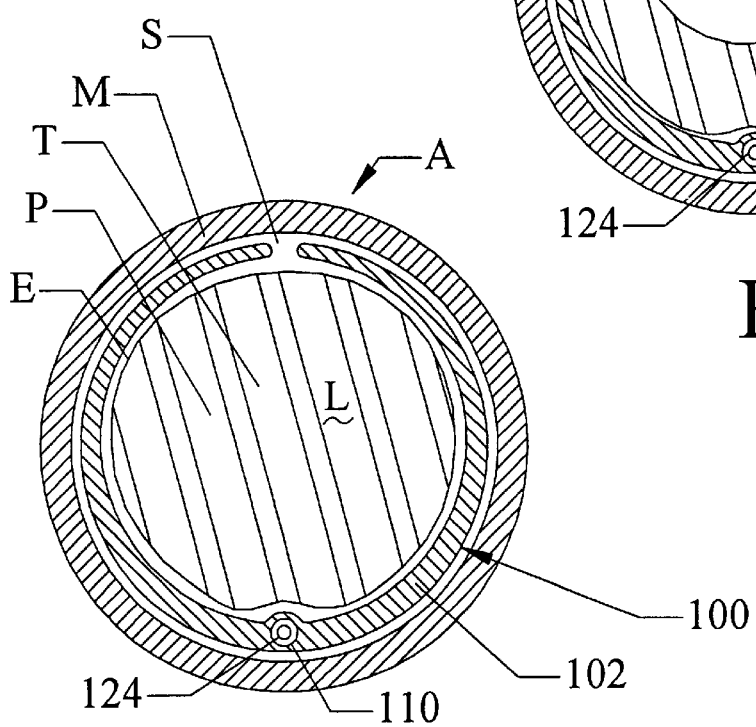

FIGS. 4A, 4B and 4C show the flexible blade dissector 100 of FIGS. 1 and 2 in use for treating an artery A using remote endarterectomy techniques. First, the artery A to the treated is surgically exposed and the arterial lumen L is opened, either by transecting the artery or making an arteriotomy incision in the wall of the artery. A plane of separation S is initiated between the atheromatous plaque P and the medial layer M by pinching the arterial wall and/or by blunt dissection using a dissecting instrument. Alternatively, in some circumstances it may be desirable to position the plane of separation S within the medial layer M or the adventitial layer or at the interface between the medial and adventitial layers of the artery A. A guidewire 124 is inserted into the plane of separation S, followed by the flexible dissecting blade 102 of the flexible blade dissector 100. The guidewire 124 helps to guide the flexible blade dissector 100 along the plane of separation S. The initial curvature of the flexible dissecting blade 102 aids in inserting the blade 102 into the plane of separation S. The guidewire 124 and the flexible dissecting blade 102 are advanced, either sequentially or simultaneously, to widen and extend the plane of separation. As the flexible blade dissector 100 is advanced, the distal edge 106 of flexible dissecting blade 102 dissects the atheromatous plaque A and the endothelial layer E away from the underlying medial layer M.

The differential stiffness of the flexible dissecting blade 102 allows it to conform to the arterial wall by bending around the central axis defined by the guidewire lumen 110 and the central ridge 112, yet it resists bending perpendicular to this axis so that the distal edge 106 of the flexible dissecting blade 102 maintains the proper orientation for effectively dissecting the plaque P along the plane of separation S. The differential stiffness of the flexible dissecting blade 102 allows the flexible blade dissector 100 to be used in arteries of different diameter. The differential stiffness of the flexible dissecting blade 102 also allows it to conform to variations in the arterial wall due to tortuosity of the artery or changes in diameter of the artery over its length.

As an illustration of this principle, FIGS. 4A, 4B and 4C show cross sections of the same flexible blade dissector 100 used in arteries of differing diameters or in different portions of the same artery. FIG. 4A shows the flexible blade dissector 100 in an artery with a diameter that closely matches the initial curvature of the flexible dissecting blade 102. The flexible dissecting blade 102 effectively removes the plaque P from approximately half of the inner circumference of the arterial lumen L at once. As the flexible blade dissector 100 advances within the artery A, the flexible dissecting blade 102 conforms to changes in the arterial wall due to tortuosity of the artery or changes in diameter of the artery over its length. For example, FIG. 4B shows the same flexible blade dissector 100 in a smaller diameter artery where the flexible dissecting blade 102 effectively removes the plaque P from approximately two-thirds of the inner circumference of the arterial lumen L at once. FIG. 4C shows the flexible blade dissector 100 in an even smaller diameter artery where the flexible dissecting blade 102 effectively removes the plaque P from the entire inner circumference of the arterial lumen L in a single pass. As an illustration of the capabilities of this endarterectomy technique, FIG. 4C shows the flexible blade dissector 100 being used to remove a total occlusion from the artery. The lumen L of the artery A may be occluded with thrombus T and/or with atherosclerotic plaque P.

In small diameter arteries, the lateral wings 114, 116 may meet edge-to-edge, as shown in FIG. 4C, or they may even overlap to accommodate to the inner diameter of the arterial lumen L. In situations, such as in FIGS. 4A and 4B, where the flexible dissecting blade does not remove the plaque P from the entire inner circumference of the arterial lumen L in a single pass, the plaque P may be entirely removed by repeated passes of the flexible dissecting blade 102. Once the plaque P has been freed from the entire inner circumference of the arterial lumen L, the plane of separation is terminated on the distal and proximal ends if necessary, and the plaque is removed from the arterial lumen L, using known techniques. Optionally, the method may utilize a separate device, such as a Moll Ring Cutter (U.S. Pat. No. 5,843,102), to terminate the plane of separation. Other techniques for accomplishing these steps are described below.

In addition to the mechanical dissection by the distal edge 106 of the flexible dissecting blade 102, dissection of the plaque P can be enhanced by supplying a pressurized fluid, such as saline solution, through the guidewire lumen 110 or through an additional lumen provided in the catheter shaft 104. The pressurized fluid may be supplied at a constant flow rate or at a varying flow rate to create a pulsating jet of fluid directed at the separation plane between the plaque P and the medial layer M of the artery A.

FIGS. 5 and 6 illustrate a coaxial system of flexible blade dissectors for performing remote endarterectomy via intraluminal techniques. A first flexible blade dissector 100, similar in construction to that shown in FIGS. 1–3, has a first flexible dissecting blade 102 mounted on a first elongated catheter shaft 104. A second flexible blade dissector 150, has a second flexible dissecting blade 152 mounted on a second elongated catheter shaft 154. The second flexible blade dissector 150 is similar in construction to that shown in FIGS. 1–3, except that the lumen 160 of the second catheter shaft 154 is large enough in diameter to insert the first catheter shaft 104 therethrough in a coaxial sliding relationship and the second flexible dissecting blade 152 is broader than the first flexible dissecting blade 102. In addition, optionally, the second flexible blade dissector 150 may be made with two distinct regions on the distal edge of the second flexible dissecting blade 152. A first, central region 156 adjacent to where the lumen 160 emerges is approximately as wide as the width of the first flexible dissecting blade 102 and is blunt and rounded. A second, outer region 158 is configured to form a dissecting edge. If desired, the coaxial system may have a third and a fourth flexible blade dissector.

Additionally, one or both of the first and second flexible blade dissectors 100, 150 may include a steering mechanism, such as those described below in connection with FIGS. 19–43, to control the direction of the flexible blade dissector 100 as it dissects a plaque from the wall of the artery.

In use, the first flexible blade dissector 100 is advanced over a guidewire 124 so that the first flexible dissecting blade 102 creates a first, narrow channel along the plane of separation between the plaque and the medial layer. Next, the second flexible blade dissector 150 is advanced over the first catheter shaft 104 so that the outer region 158 of the second flexible dissecting blade 152 widens the channel. The central region 156 of the second flexible dissecting blade 152, being blunt and rounded, tends to follow the premade channel created by the first flexible dissecting blade 102. This helps to keep the second flexible blade dissector 150 on a predetermined path, while the second flexible dissecting blade 152 sequentially widens the channel. This process may be continued with any additional coaxial flexible blade dissectors, if necessary, until the plaque has been freed from the entire inner circumference of the arterial lumen.

Figure 8:
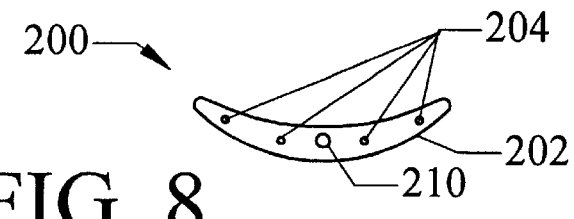
FIGS. 7, 8 and 9 show a flexible blade dissector having a flexible dissecting blade with internal longitudinal stiffeners to enhance the differential stiffness.
Figure 7:
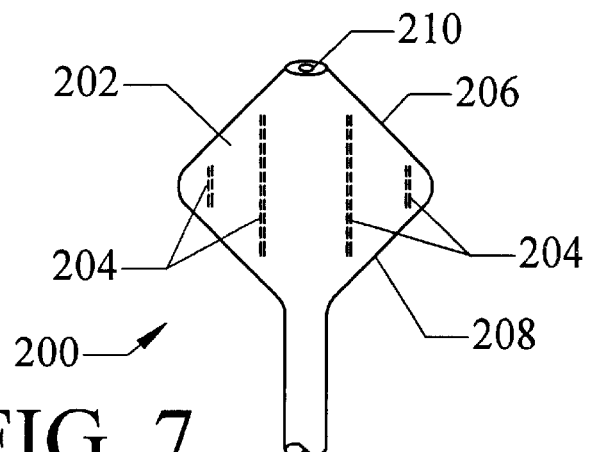
Figure 9:
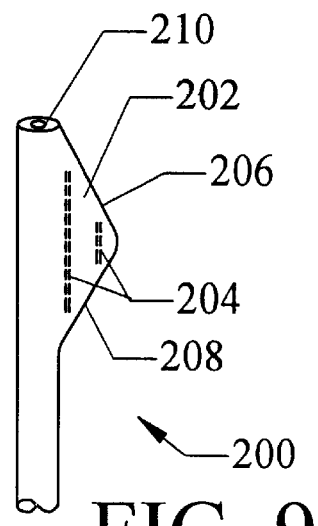

Additional structure can be used to enhance the differential stiffness of the flexible blade dissector and its ability to conform to variations in the arterial wall due to tortuosity of the artery or changes in diameter of the artery over its length. FIGS. 7, 8 and 9 show a flexible blade dissector 200 having a flexible dissecting blade 202 with internal longitudinal stiffeners 204 to enhance the differential stiffness. FIG. 7 is a front view, FIG. 8 is a distal end view and FIG. 9 is a side view of a distal portion of the flexible blade dissector 200. The flexible dissecting blade 202 is made of a highly flexible polymer or elastomer, for example a low durometer PEBAX polyamide elastomer resin (ATOCHEM SA, France). Embedded within the flexible dissecting blade 202 are a multiplicity of internal longitudinal stiffeners 204, shown as hidden lines in FIGS. 7 and 9. The internal longitudinal stiffeners 204 may be made of metal wire, such as stainless steel or a nickel-titanium alloy, or a stiff fiber, such as glass fiber, carbon fiber or a rigid polymer. The internal longitudinal stiffeners 204 are arranged roughly parallel to the central axis defined by the guidewire lumen 210 of the flexible blade dissector 200. The internal longitudinal stiffeners 204 may run substantially the fall length of the flexible dissecting blade 202 from the distal edge 206 to the proximal edge 208. Alternatively, the internal longitudinal stiffeners 204 may comprise a multiplicity of short wires or fibers arranged in a pattern that enhances the differential stiffness of the flexible dissecting blade 202. The arrangement of the internal longitudinal stiffeners 204 enhances the differential stiffness of the flexible dissecting blade 202, allowing it to bend around the central axis defined by the guidewire lumen 210, but resisting bending perpendicular to the central axis.

Figure 11:
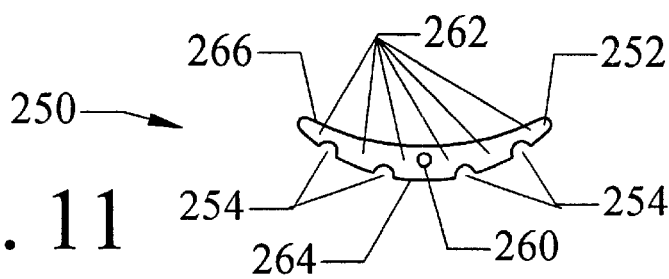
FIGS. 10 and 11 show another flexible blade dissector having a flexible dissecting blade with longitudinal grooves to enhance the differential stiffness.
Figure 10:
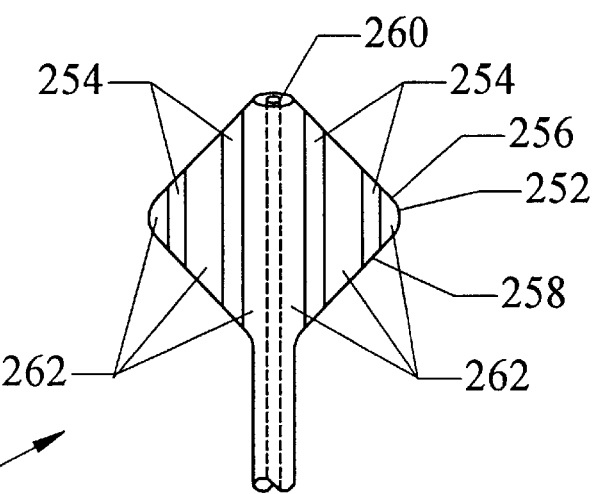

FIGS. 10 and 11 show another flexible blade dissector 250 having a flexible dissecting blade 252 with longitudinal grooves 254 to enhance the differential stiffness. FIG. 10 is a front view and FIG. 11 is a distal end view of a distal portion of the flexible blade dissector 250. The flexible dissecting blade 252 is made of a flexible polymer or elastomer, for example a PEBAX polyamide elastomer resin. Formed in the surface of the flexible dissecting blade 252 are a multiplicity of longitudinal grooves 254. The longitudinal grooves 254 may run substantially the full length of the flexible dissecting blade 252 from the distal edge 256 to the proximal edge 258, as shown, or a multiplicity of shorter grooves may be arranged in a pattern that enhances the differential stiffness of the flexible dissecting blade 252. The longitudinal grooves 254 may be formed in the convex surface 264 or the concave surface 266 of the flexible dissecting blade 252 or in both surfaces. The flexible dissecting blade 252 between the longitudinal grooves 254 forms a multiplicity of longitudinal ribs 262 that enhance the longitudinal stiffness, while the longitudinal grooves 254 enhance the lateral flexibility. This arrangement enhances the differential stiffness of the flexible dissecting blade 252, allowing it to bend around the central axis defined by the guidewire lumen 260, but resisting bending perpendicular to the central axis. In an alternate construction method, the alternating longitudinal grooves 254 and longitudinal ribs 262 may be formed by laminating separate longitudinal ribs 262 onto a thin, flexible dissecting blade 252 to enhance the differential stiffness. If desired, the longitudinal ribs 262 and the flexible dissecting blade 252 may be made of different materials to further enhance the differential stiffness. With either construction method, the differential stiffness keeps the distal edge 256 of the flexible dissecting blade 252 in the proper orientation for dissecting the plaque away from the underlying medial layer, while it allows the flexible dissecting blade 252 to flex laterally in order to adjust to the internal diameter of the arterial lumen.

Additionally, the longitudinal grooves 254 may be filled with a softer material than the flexible dissecting blade 252 is made from to enhance the differential stiffness, while presenting a smooth outer surface on both the convex surface 264 and the concave surface 266 of the flexible dissecting blade 252. Alternatively, the longitudinal grooves 254 may covered over with an outer skin (not shown) to create voids within the flexible dissecting blade 252 to enhance the differential stiffness, or voids may be molded into the flexible dissecting blade 252 to enhance the differential stiffness.

Figure 13:
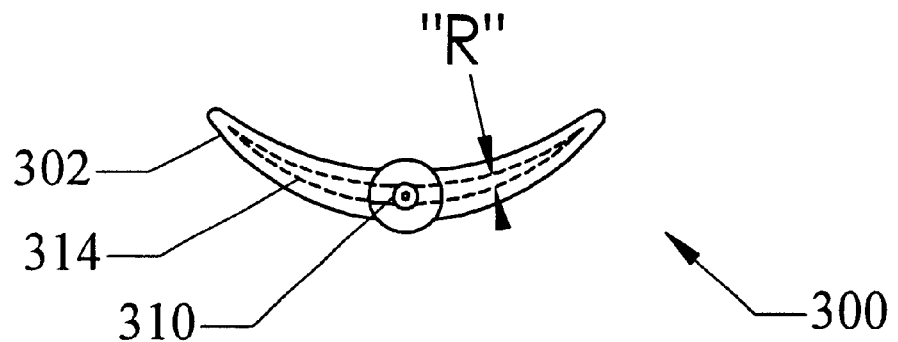
FIGS. 12 and 13 show another flexible blade dissector having a flexible dissecting blade with an internal stiffener at the leading edge to enhance the differential stiffness.
Figure 12:
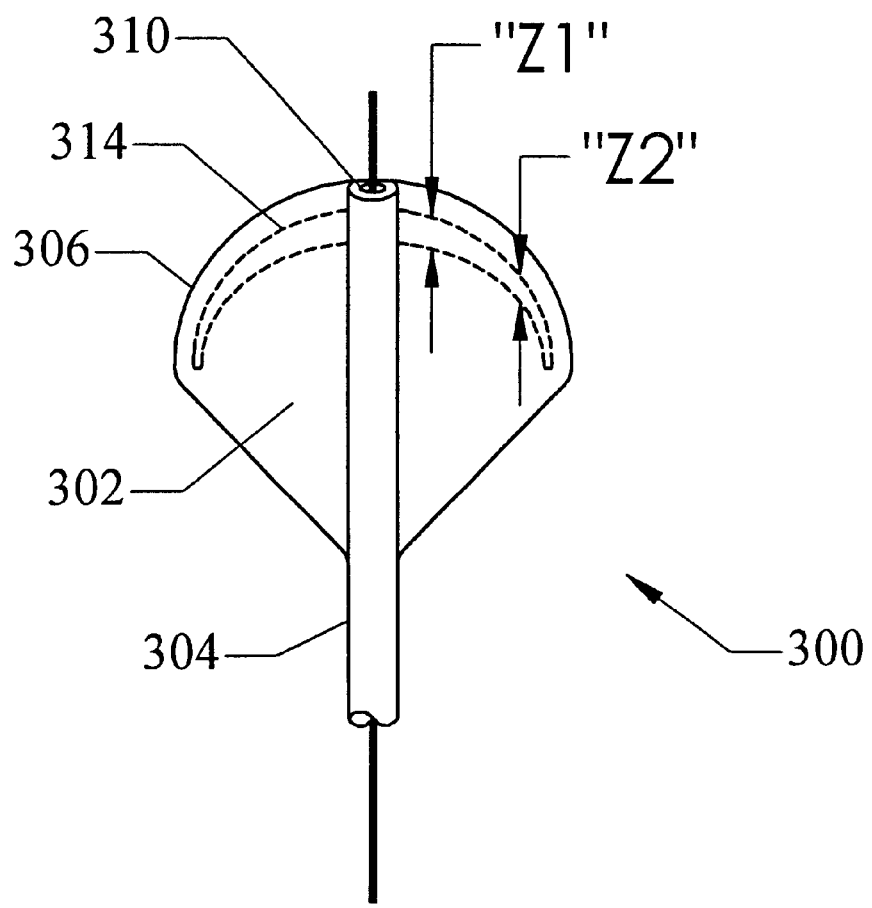

FIGS. 12 and 13 show another flexible blade dissector 300 having a flexible dissecting blade 302 with an internal stiffener 314 at the leading edge to enhance the differential stiffness. FIG. 12 is a front view and FIG. 13 is a distal end view of a distal portion of the flexible blade dissector 300. The flexible dissecting blade 302 is made of a flexible polymer or elastomer, for example a PEBAX polyamide elastomer resin. Embedded in the flexible dissecting blade 302, close to the distal edge 306, is an internal stiffener 314. The internal stiffener 314 may be made in one piece or in two pieces and is preferably attached to the catheter shaft 304 so that pushing force is transmitted from the catheter shaft 304 directly to the internal stiffener 314. The internal stiffener 314 may be made of a metal, such as stainless steel or a nickel-titanium alloy, a rigid polymer, or a stiff fabric, such as a glass fiber or carbon fiber fabric. The internal stiffener 314 has a thickness R and a width Z, measured parallel with the central axis defined by the guidewire lumen 310, and a length measured perpendicular to the central axis. Preferably, the length of the internal stiffener 314 is substantially equal to the width of the flexible dissecting blade 302 and closely conforms to the distal edge 306, which in this exemplary embodiment approximates a semicircular are. If desired, the width Z may taper along the length of the internal stiffener 314, as illustrated by the difference between Z1 and Z2 in FIG. 12, making the internal stiffener 314 approximately crescent shaped in this example. Preferably, the width Z is substantially greater than the thickness R so that the internal stiffener 314 and the flexible dissecting blade 302 will preferentially bend around the central axis, but will resist bending about an axis perpendicular to the central axis, enhancing the differential stiffness of the flexible dissecting blade 302. Preferably, the internal stiffener 314 and the flexible dissecting blade 302 are made with an initial curvature, as seen in the distal end view of FIG. 13. Typically, the internal stiffener 314 will be made of a resilient, elastic material, however in some cases it may be desirable to make the internal stiffener 314 of a malleable material so that the flexible dissecting blade 302 can be bent to a desired curve or shape.

Figures 15, 16:
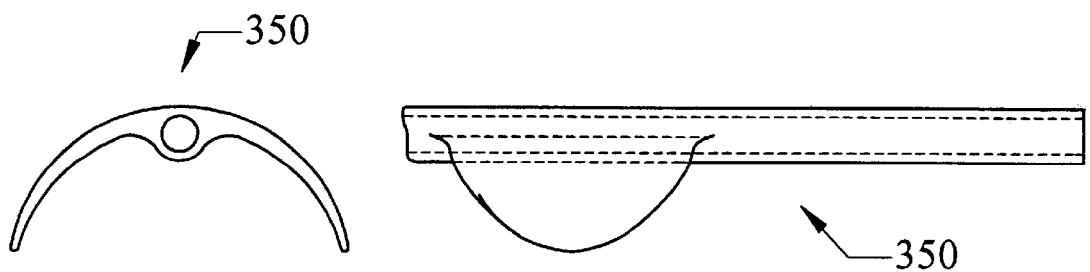
FIGS. 14, 15, 16, 17 and 18 show another flexible blade dissector illustrating an alternate geometry for the flexible dissecting blade.
Figures 14, 17:
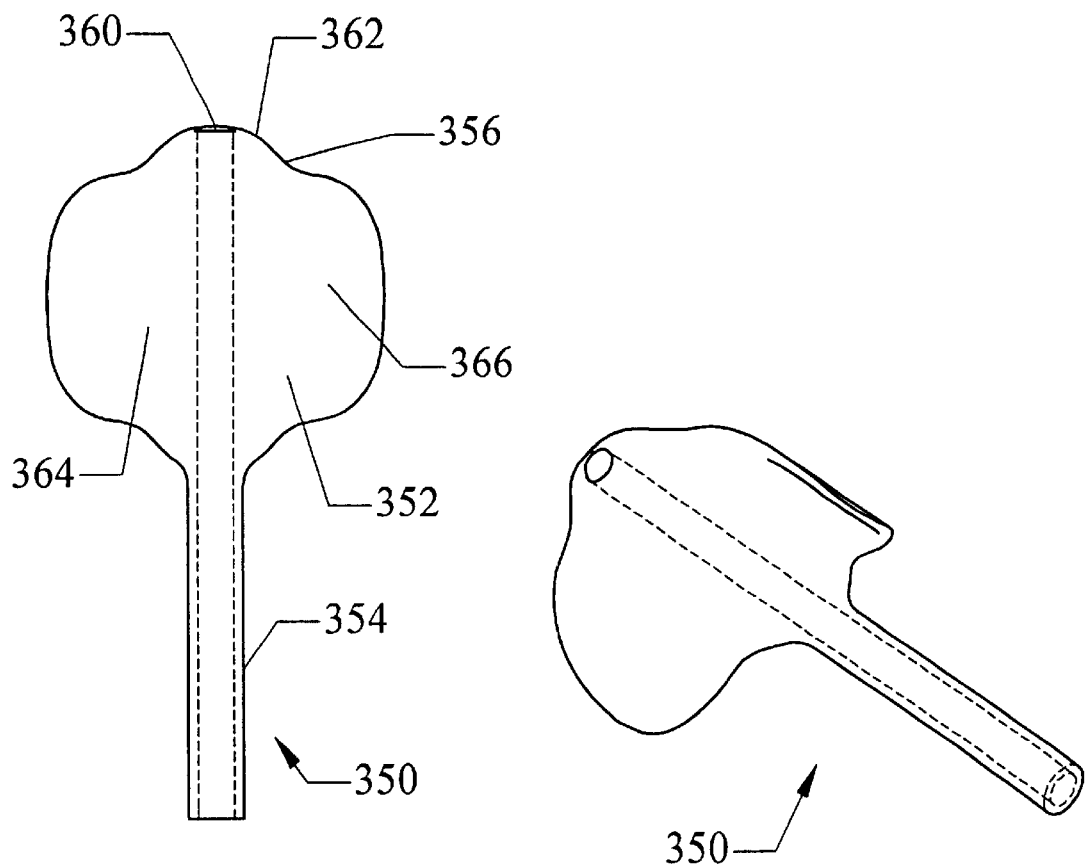

FIGS. 14, 15, 16 and 17 show another flexible blade dissector 350 illustrating an alternate geometry for the flexible dissecting blade 352. FIG. 14 is a front view, FIG. 15 is a distal end view, FIG. 16 is a side view and FIG. 17 is a perspective view of a distal portion of the flexible blade dissector 350 with the flexible dissecting blade 352 mounted on a catheter shaft 354 with a guidewire lumen 360. In this illustrative embodiment, the distal edge 356 of the flexible dissecting blade 352 has a nose 362 that extends distally beyond the lateral wings 364, 366 of the flexible dissecting blade 352. The nose 362 of the flexible dissecting blade 352 is convex or semicircular, as seen from the front view of FIG. 14, and serves as an advance dissector to create a path along the separation plane between the plaque and the underlying medial layer for the wider lateral wings 364, 366 to follow. This creates a two-stage dissecting effect, similar to the coaxial system of FIGS. 5 and 6, using a single flexible blade dissector 350. Alternatively, this flexible blade dissector 350 can be used very effectively as the second flexible blade dissector 150 in the coaxial system of FIGS. 5 and 6. For this purpose, the nose 362 of the flexible dissecting blade 352 may be made with a blunt and rounded distal edge 356. The geometry of the flexible dissecting blade 352 gives it the desired differential stiffness characteristics. The differential stiffness may be further enhanced using any of the constructions described above in connection with FIGS. 7–12.

In each of the embodiments described above, the flexible dissecting blade has been made symmetrical. This has the advantage that, in a uniform plaque, a symmetrical dissecting blade will tend to track straight and parallel to the longitudinal axis of the artery. However, in a non-uniform plaque, the resultant forces on a symmetrical dissecting blade may be unbalanced, causing the dissecting blade to veer to the side, taking the path of least resistance. When these conditions can be foreseen, the flexible dissecting blade may be made asymmetrical to compensate to balance the forces so that the dissecting blade will tend to track straight through the non-uniform plaque. However, it is more likely that such conditions will not be foreseen prior to encountering them in a clinical situation. For such situations, it would be beneficial to be able to control the direction of the flexible dissecting blade as it dissects a plaque from the wall of the artery.

FIGS. 18–42 show various means of steering the flexible dissecting blade 102 to control the direction of the flexible blade dissector 100 as it dissects a plaque from the wall of the artery. Various steering strategies can be used to direct the flexible dissecting blade 102 to the right or to the left within a plane of dissection andor to direct the flexible dissecting blade 102 outward or inward to change the depth of the plane of dissection within the arterial wall. Three possible steering strategies, characterized as neck-based steering, nose-based steering and wing-based steering, are described below. These three steering strategies can be used separately or in combination with one another. Various steering mechanisms can be incorporated into the flexible blade dissector 100 to implement these steering strategies.

FIGS. 18–29 show a flexible blade dissector 100 with neck-based steering. The flexible blade dissector 100 has a bendable neck 130 on the elongated catheter shaft 104 just proximal to the flexible dissecting blade 102. The flexible blade dissector 100 can be steered by bending the catheter shaft 104 at the neck 130 to direct the flexible dissecting blade 102 to the left or right and/or outward or inward with respect to the arterial wall.

Figure 18:
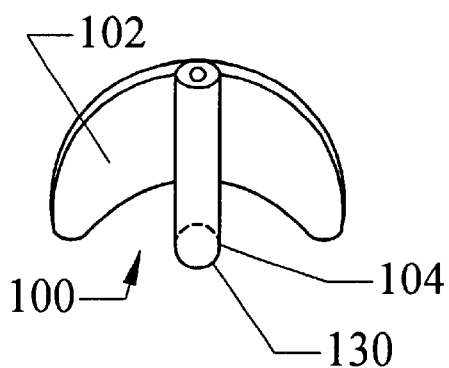
Figure 19:
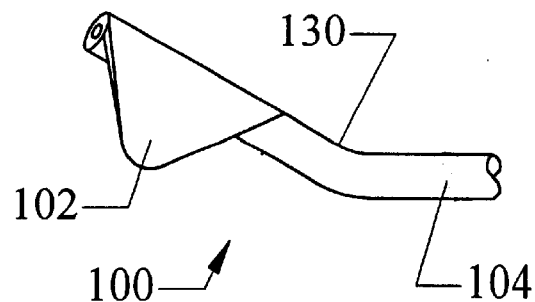
FIGS. 19–23 show the application of neck-based steering for controlling the radial position of the flexible dissecting blade with respect to the arterial wall.
Figure 20:
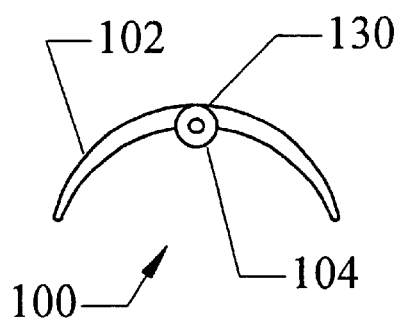
Figure 21:
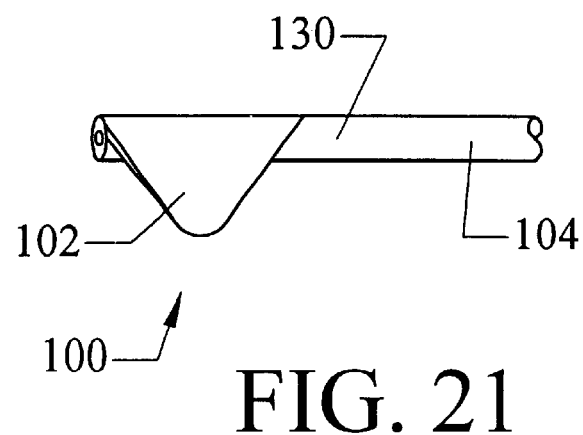
Figure 22:
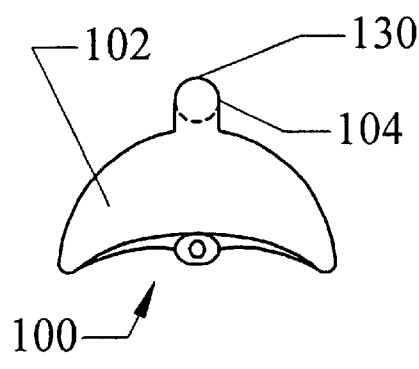
Figure 23:
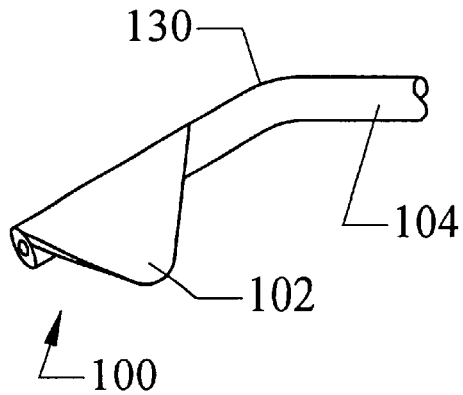

FIGS. 18–23 show the application of neck-based steering for controlling the radial position of the flexible dissecting blade 102 with respect to the arterial wall. FIGS. 18 and 19 show a distal end view and a side view, respectively, of the flexible dissecting blade 102 angulated outward with respect to the arterial wall to direct the plane of separation deeper toward the medial and adventitial layers of the arterial wall. FIGS. 20 and 21 show a distal end view and a side view of the flexible dissecting blade 102 steering straight. FIGS. 22 and 23 show a distal end view and a side view of the flexible dissecting blade 102 angulated inward with respect to the arterial wall to direct the plane of separation toward the endothelial layer of the arterial wall.

Figure 28:
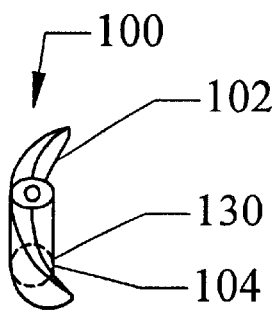
FIGS. 24–29 show the application of neck-based steering for controlling the lateral position of the flexible dissecting blade with respect to the arterial wall.
Figure 29:
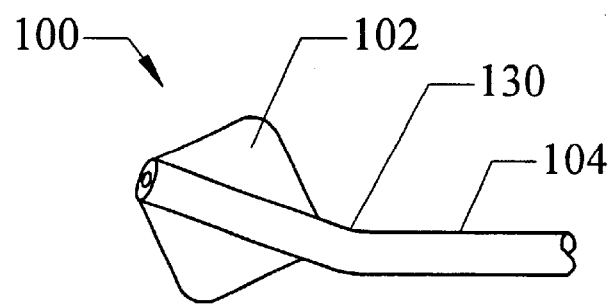
Figure 26:
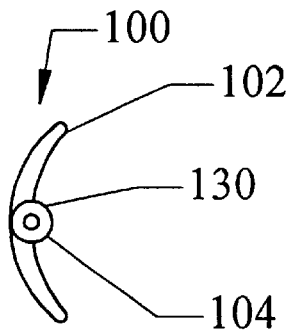
Figure 27:
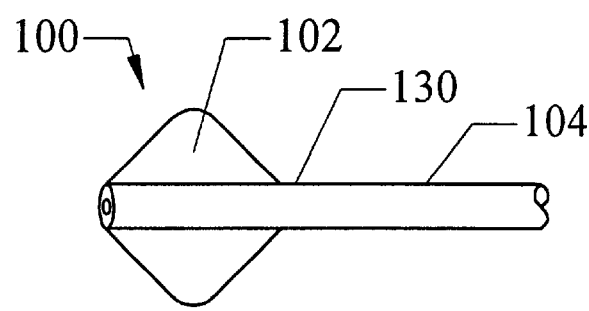
Figure 24:
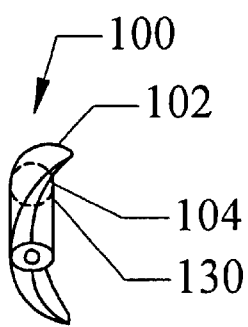
Figure 25:
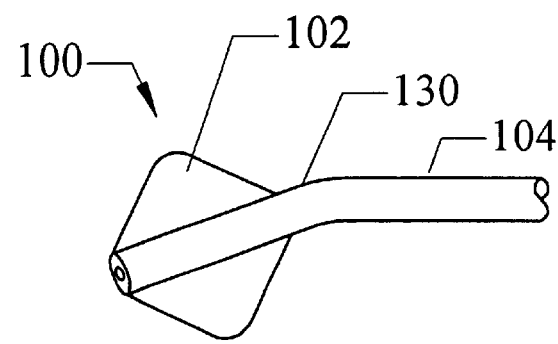

FIGS. 24–29 show the application of neck-based steering for controlling the lateral position of the flexible dissecting blade 102 with respect to the arterial wall. FIGS. 24 and 25 show a distal end view and a radial inside view of the underside of the flexible blade dissector 100, as if viewing the device from within the arterial lumen, with the flexible dissecting blade 102 steering toward the right from the catheter's frame of reference within the arterial wall. FIGS. 26 and 27 show a distal end view and a radial inside view of the flexible dissecting blade 102 steering straight. FIGS. 28 and 29 show a distal end view and a radial inside view of the flexible dissecting blade 102 steering toward the left from the catheter's frame of reference within the arterial wall.

Figure 30:
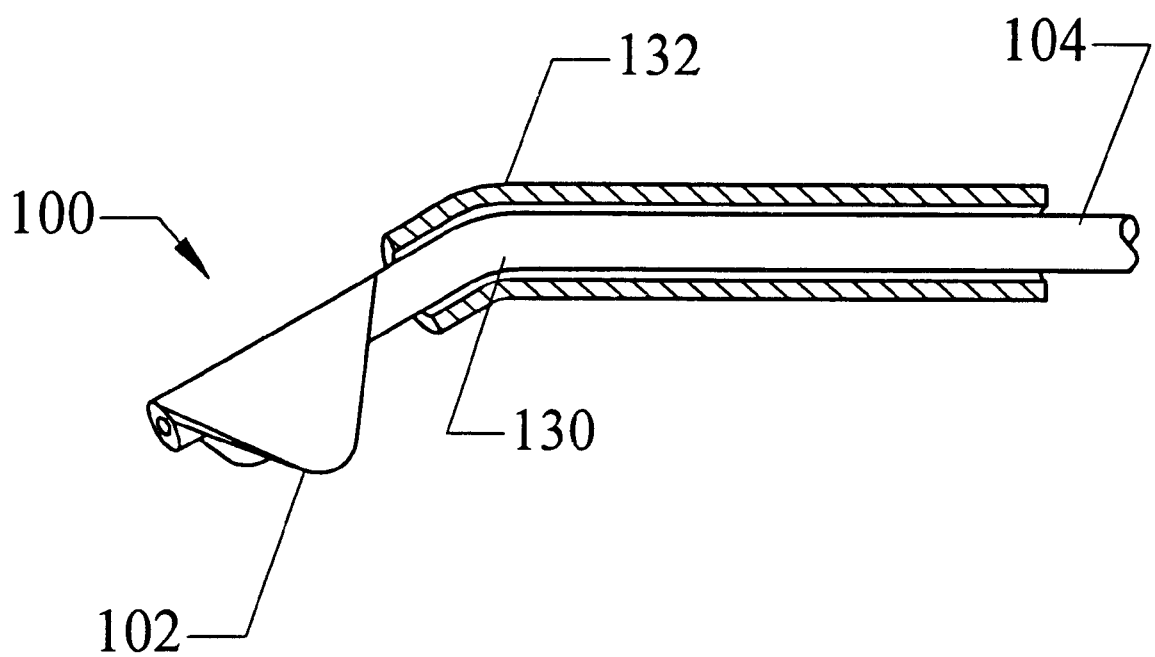
FIG. 30 shows an embodiment of the flexible blade dissector having neck-based steering provided by a rotatable external guide catheter for controlling the direction of the catheter shaft.

Various steering mechanisms can be used to implement the neck-based steering strategy. FIG. 30 shows an embodiment of the flexible blade dissector 100 having neck-based steering provided by a rotatable external guide catheter 132 for controlling the direction of the catheter shaft. The external guide catheter 132 may be preformed into a curve or it may be malleable or heat formable at the point of use. Alternatively, the neck-based steering strategy can implemented using an internal steering tube, as described below in connection with FIG. 32, or using control wires, as described below in connection with FIGS. 33–38.

Figure 31:
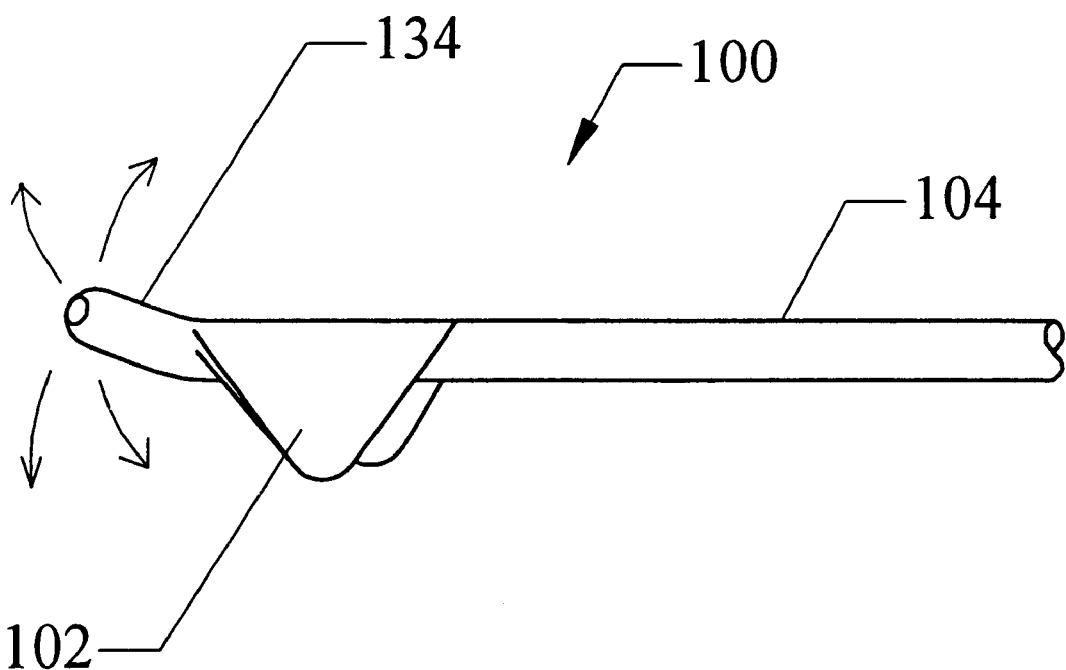
FIG. 31 shows the application of nose-based steering for controlling the radial position and lateral position of the flexible dissecting blade with respect to the arterial wall.

FIG. 31 shows the application of nose-based steering for controlling the radial position and lateral position of the flexible dissecting blade 102 with respect to the arterial wall. The flexible blade dissector 100 is made with a movable nose 134 at the distal end of the catheter shaft 104. The movable nose 134 may be integral with the flexible dissecting blade 102 or it may extend distally of the flexible dissecting blade 102, as shown in this exemplary embodiment. The movable nose 134 acts as a blunt dissecting probe for extending the plane of dissection in a desired direction within the arterial wall for the flexible dissecting blade 102 to follow. The movable nose 134 can be flexed up and down to direct the flexible dissecting blade 102 radially outward or inward with respect to the arterial wall. The movable nose 134 can also be flexed to the left and right to direct the flexible dissecting blade 102 left or right within the arterial wall.

Figure 32:
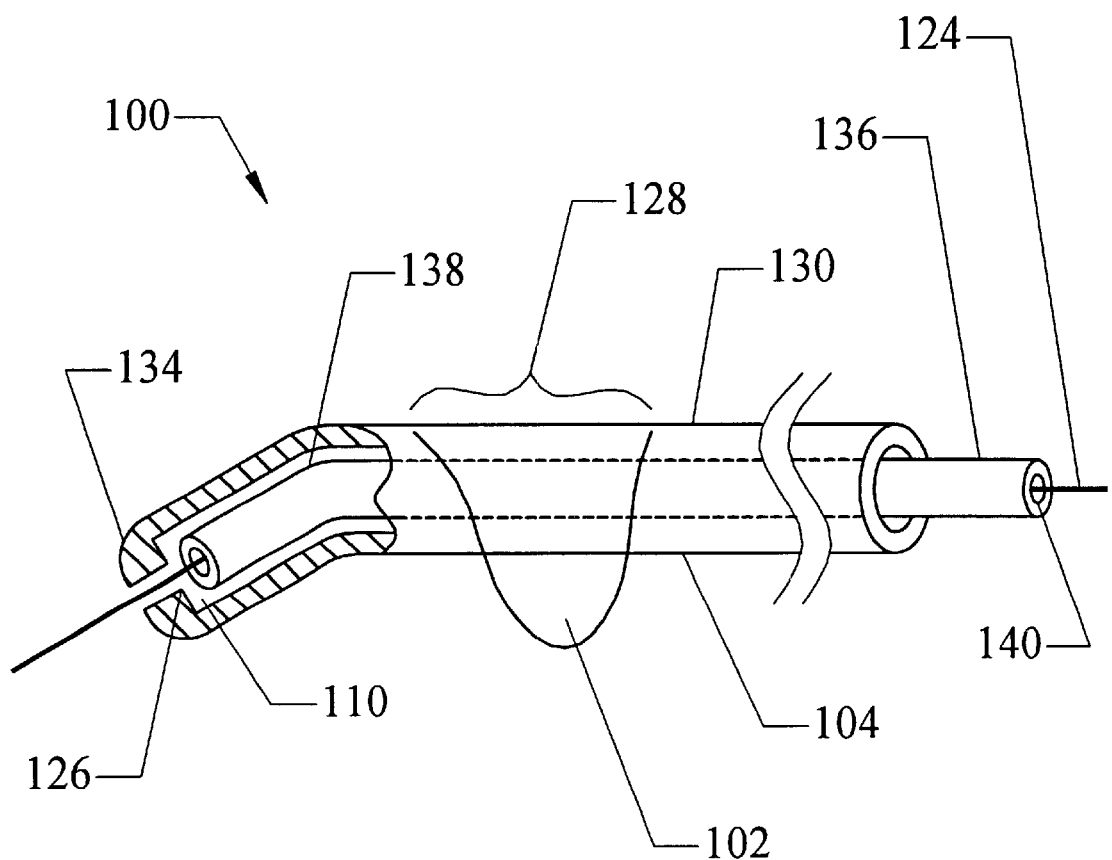
FIG. 32 shows an embodiment of the flexible blade dissector having nose-based steering provided by a rotatable internal steering tube within the catheter shaft.

FIG. 32 shows a cutaway view of an embodiment of the flexible blade dissector 100 having nose-based steering provided by a rotatable internal steering tube 136 within the lumen 110 of the catheter shaft 104. The internal steering tube 136 may be preformed into a curve or bend 138 or it may be malleable or heat formable at the point of use. The internal steering tube 136 may be constructed of metals, such as stainless steel or a superelastic nickel-titanium alloy, polymers or a composite construction, for example a fiber reinforced or wire braided composite or a coil reinforced andor counterwound torque tube. Preferably, the internal steering tube 136 includes an internal guidewire lumen 140 for passage of a guidewire 124. Alternatively, the internal steering tube 136 may be replaced with a solid stylet that is precurved and/or malleable so that the user can create the desired curve at the point of use.

For nose-based steering, the internal steering tube 136 is inserted into the lumen 110 of the catheter shaft 104 until the bend 138 is positioned within the movable nose 134 of the flexible blade dissector 100. If desired, an internal shoulder 126 may be provided near the distal end of the lumen 110 to prevent the steering tube 136 from being inserted beyond the distal end of the catheter shaft 104. The steering tube 136 is rotated from its proximal end to steer the movable nose 134 of the flexible blade dissector 100 in the desired direction. Neck-based steering and wing-based steering can also be implemented using an internal steering tube 136 by inserting or withdrawing the internal steering tube 136 until the bend 138 is positioned at the bendable neck 130 or the wing region 128 of the catheter shaft 104. Alternatively, the nose-based steering strategy can implemented using control wires, as described below in connection with FIGS. 33–38.

Figure 33:
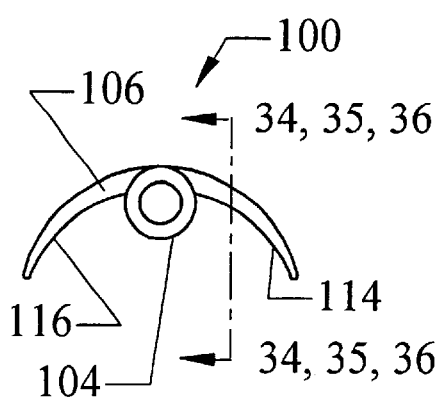
FIGS. 33–36 show the application of wing-based steering for controlling the radial position and the lateral position of the flexible dissecting blade with respect to the arterial wall.
Figure 34:
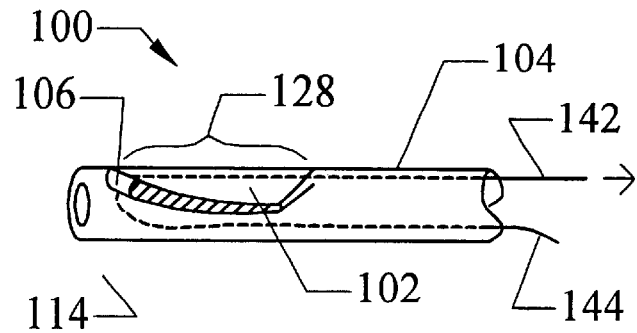
Figure 35:
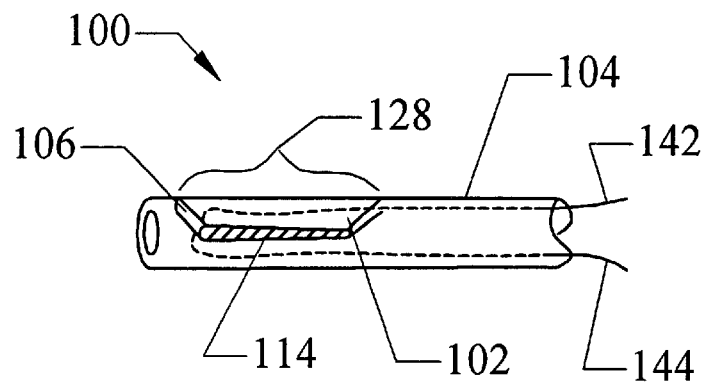
Figure 36:
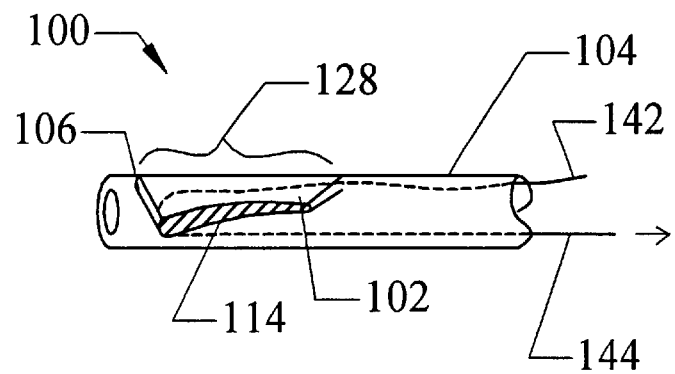

FIGS. 33–38 show the application of wing-based steering utilizing control wires for controlling the radial position and the lateral position of the flexible dissecting blade 102 with respect to the arterial wall. FIG. 33 shows a distal end view of the flexible blade dissector 100. FIGS. 34, 35 and 36 are side views of the flexible blade dissector 100 cut away along the section line shown in FIG. 33. The flexible blade dissector 100 includes an upper control wire 142 and a lower control wire 144 that extend through the catheter shaft 104 from the proximal end and attach to the wings 114, 116 of the flexible dissecting blade 102 (or to the wing region 128 of the catheter shaft 104 in the vicinity of the flexible dissecting blade 102). The upper control wire 142 is attached near the top of the leading edge 106 of the flexible dissecting blade 102 and the lower control wire 144 is attached near the bottom of the leading edge 106 of the flexible dissecting blade 102. In FIG. 34, the upper control wire 142 has been pulled from its proximal end to angle or curve the flexible dissecting blade 102 upward to steer the flexible blade dissector 100 radially outward with respect to the arterial wall. In FIG. 35, no steering is applied. In FIG. 36, the lower control wire 144 has been pulled from its proximal end to angle or curve the flexible dissecting blade 102 downward to steer the flexible blade dissector 100 radially inward with respect to the arterial wall. If desired, additional control wires may be provided for individually controlling the upward and downward pitch of the wings 114, 116 of the flexible dissecting blade 102.

Figure 37:
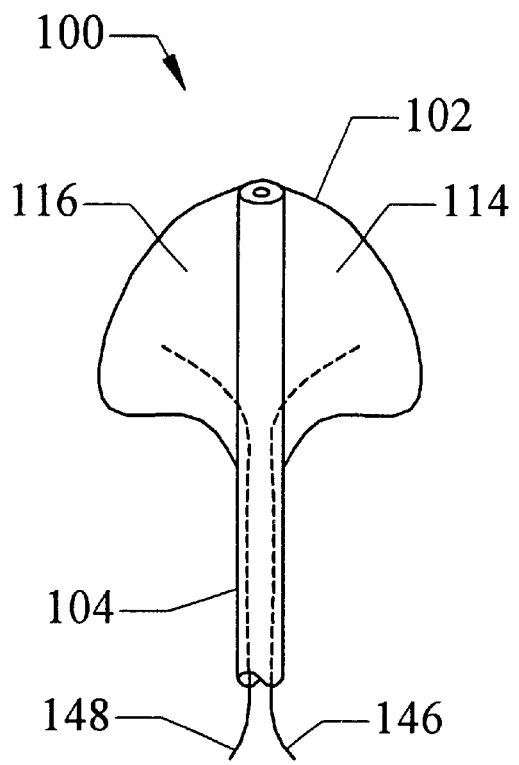
FIGS. 37–38 show an embodiment of the flexible blade dissector having wing-based steering provided by a pull wires connected to the wings of the flexible dissecting blade.
Figure 38:
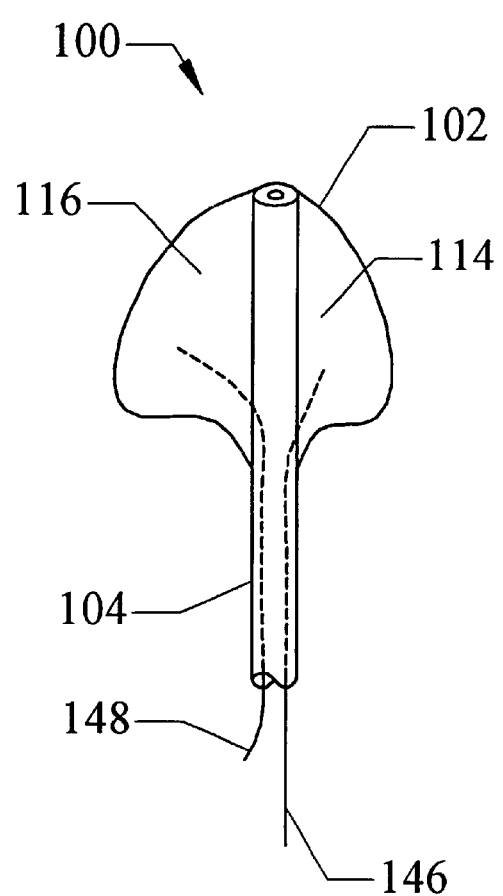

FIGS. 37 and 38 are underside views of the flexible blade dissector 100 showing a left control wire 146 attached to the left wing 114 from the catheter's frame of reference and a right control wire 148 attached to the right wing 116 of the flexible dissecting blade 102. In FIG. 37, no steering is applied and the flexible dissecting blade 102 will travel straight along the dissecting plane within the arterial wall. In FIG. 38, the left control wire 146 has been pulled from its proximal end to angle or curve the flexible dissecting blade 102 toward the left with respect to the arterial wall. Depending on the relative stiffness of the wings 114, 116 of the flexible dissecting blade 102 and the catheter shaft 104, the flexible blade dissector 100 may also exhibit some degree of neck-based steering when the control wires 146, 148 are pulled.

Alternatively, the control wires 142, 144, 146, 148 may be attached to the catheter shaft 104 or to the nose 134 of the flexible blade dissector 100 to implement neck-based or nose-based steering, as described above.

Figure 39:
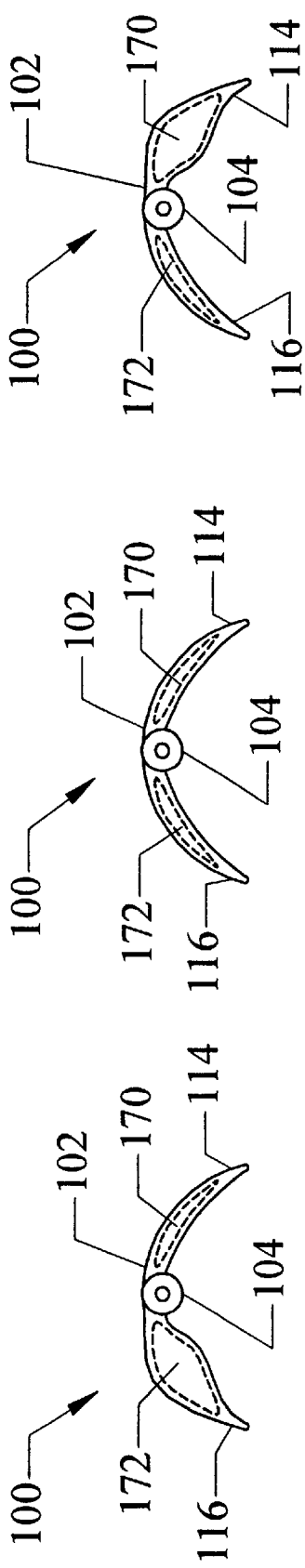
FIGS. 39–42 show an embodiment of the flexible blade dissector having wing-based steering provided by inflatable chambers within the wings of the flexible dissecting blade.
Figure 40:
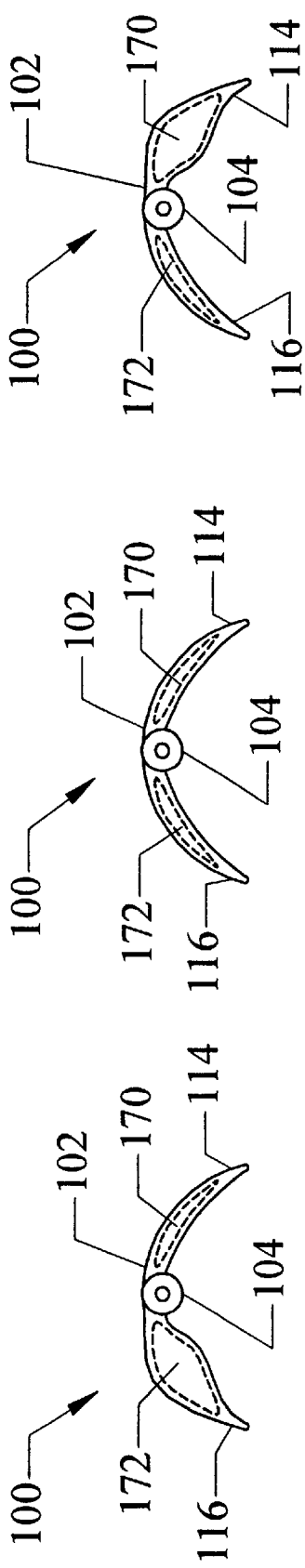
Figure 41:
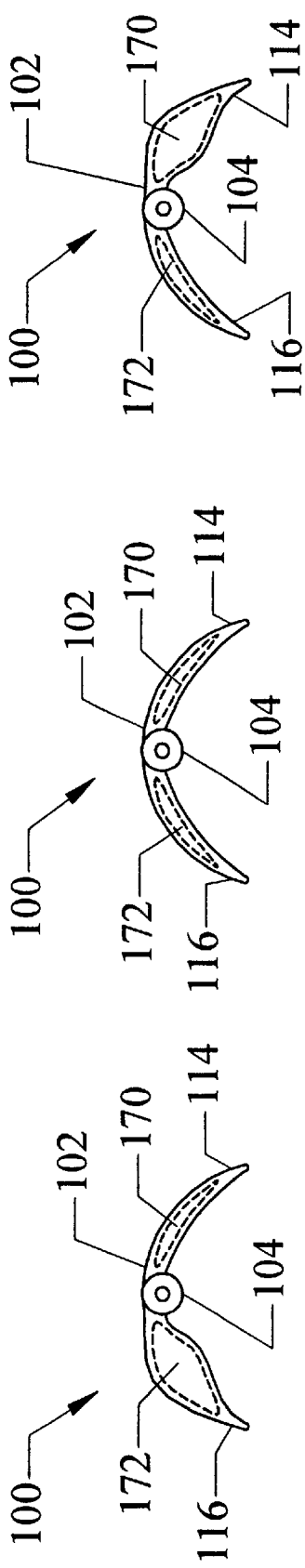
Figure 42:
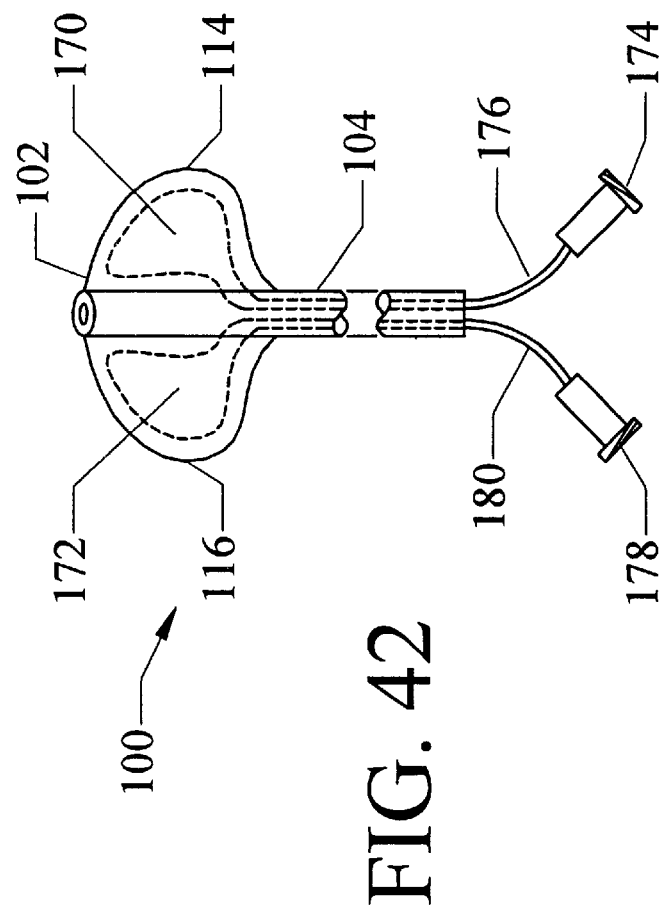

FIGS. 39–42 show an embodiment of the flexible blade dissector 100 having wing-based steering provided by inflatable chambers 170, 172 within the wings 114, 116 of the flexible dissecting blade 102. FIG. 42 is an underside view of the flexible blade dissector 100. A left side inflatable chamber 170 located in the left wing 114 is connected to a left inflation fitting 174 by a left inflation lumen 176 that extends through the catheter shaft 104, and a right side inflatable chamber 172 located in the right wing 116 is connected to a right inflation fitting 178 by a right inflation lumen 180. FIG. 39 is a lateral cross section of the flexible dissecting blade 102 with the right side inflatable chamber 172 inflated with saline solution or the like. When inflated, the right wing 116 will have greater drag force on it as the device is advanced and the flexible dissecting blade 102 will steer to one side. FIG. 41 is a lateral cross section of the flexible dissecting blade 102 with the left side inflatable chamber 174 inflated with saline solution or the like. When inflated, the left wing 114 will have greater drag force on it as the device is advanced and the flexible dissecting blade 102 will steer to the other side. In FIG. 40, both of the inflatable chambers 170, 172 are deflated and the flexible dissecting blade 102 will steer straight along the dissecting plane within the arterial wall.

Alternatively or in addition, the inflatable chambers 170, 172 may also be used to propagate the dissection of the plaque from the artery wall. The inflatable chambers 170, 172 may be inflated separately or together to create a dilating force to separate the plaque from the artery wall.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An endarterectomy device, comprising:
    an elongated shaft having a proximal end and a distal end; and
    a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;
wherein said flexible dissecting blade has a central ridge oriented parallel to said elongated shaft, a left lateral wing extending to the left of said central ridge and terminating in a left lateral edge and a right lateral wing extending to the right of said central ridge and terminating in a right lateral edge, said left lateral wing having a tapered thickness that tapers down from said central ridge to said left lateral edge and said right lateral wing having a tapered thickness that tapers down from said central ridge to said right lateral edge.

2. The endarterectomy device of claim 1, wherein said flexible dissecting blade has a preset initial curvature, wherein said flexible dissecting blade is curved about an axis parallel to said elongated shaft.

3. The endarterectomy device of claim 1, further comprising an internal lumen extending from said proximal end to said distal end of said elongated shaft.

4. The endarterectomy device of claim 3, further comprising a guidewire sized and configured for passage through said internal lumen of said elongated shaft.

5. An endarterectomy device, comprising:
    an elongated shaft having a proximal end and a distal end; and
    a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;
wherein said flexible dissecting blade has a plurality of longitudinally oriented stiffeners embedded within said flexible dissecting blade for enhancing the differential stiffness of said flexible dissecting blade.

6. An endarterectomy device, comprising:
    an elongated shaft having a proximal end and a distal end; and
    a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;
wherein said flexible dissecting blade has a plurality of longitudinally oriented grooves for enhancing the differential stiffness of said flexible dissecting blade.

7. An endarterectomy device, comprising:
    an elongated shaft having a proximal end and a distal end; and
    a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;
wherein said flexible dissecting blade has at least one laterally oriented stiffener for enhancing the differential stiffness of said flexible dissecting blade.

8. The endarterectomy device of claim 1, wherein said flexible dissecting blade is approximately diamond shaped.

9. The endarterectomy device of claim 1, further comprising a steering mechanism for directing said endarterectomy device within the vascular wall.

10. An endarterectomy device, comprising:
    an elongated shaft having a proximal end and a distal end; and
    a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis; and
    a steering mechanism for directing said endarterectomy device within the vascular wall, wherein said steering mechanism comprises a movable nose extending distally from said flexible dissecting blade.

11. An endarterectomy device, comprising:

an elongated shaft having a proximal end and a distal end; and a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis; and a steering mechanism for directing said endarterectomy device within the vascular wall, wherein said steering mechanism comprises a bendable neck on said elongated shaft proximal to said flexible dissecting blade.

12. An endarterectomy device, comprising:

an elongated shaft having a proximal end and a distal end; and a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis; and a steering mechanism for directing said endarterectomy device within the vascular wall, wherein said steering mechanism is configured to change the geometry of said flexible dissecting blade for directing said endarterectomy device within the vascular wall.

13. An endarterectomy device, comprising:

an elongated shaft having a proximal end and a distal end; and a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis; and a steering mechanism for directing said endarterectomy device within the vascular wall, wherein said steering mechanism comprises a first control wire for angulating said flexible dissecting blade in a first direction and a second control wire for angulating said flexible dissecting blade in a second direction.

14. An endarterectomy device, comprising:

an elongated shaft having a proximal end and a distal end; and a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;

wherein said flexible dissecting blade comprises at least one inflatable chamber.

15. An endarterectomy device, comprising:

an elongated shaft having a proximal end and a distal end; and a flexible dissecting blade mounted at said distal end of said elongated shaft, said flexible dissecting blade having a distal edge configured for dissecting a plane of separation between an atherosclerotic plaque and a layer of a vascular wall, said flexible dissecting blade having differential stiffness, wherein said flexible dissecting blade has a greater flexibility about a longitudinal axis parallel to said elongated shaft and greater resistance to bending about a lateral axis perpendicular to said longitudinal axis;

wherein said flexible dissecting blade comprises lateral wings extending to the left and right of said elongated shaft, a first inflatable chamber within the left lateral wing and a second inflatable chamber within the right lateral wing of said flexible dissecting blade.

16. An endarterectomy device, comprising:

a first flexible blade dissector having a first elongated shaft having a proximal end and a distal end, and a first flexible dissecting blade mounted at said distal end of said first elongated shaft, said first flexible dissecting blade having a distal edge configured for dissecting a plane of separation between an atherosclerotic plaque and a vascular wall; and a second flexible blade dissector having a second elongated shaft having a proximal end and a distal end, an internal lumen extending from said proximal end to said distal end of said second elongated shaft, said internal lumen being sized and configured for passage of said first elongated shaft therethrough, and a second flexible dissecting blade mounted at said distal end of said second elongated shaft.

17. The endarterectomy device of claim 16, wherein said second flexible dissecting blade has a width greater than said first flexible dissecting blade.

18. The endarterectomy device of claim 17, wherein said second flexible dissecting blade has a distal edge having a central region and an outer region, wherein at least said outer region of said distal edge is configured for dissecting a plane of separation between the atherosclerotic plaque and the vascular wall.

19. The endarterectomy device of claim 16, wherein said first elongated shaft comprises an internal lumen extending from said proximal end to said distal end of said first elongated shaft.

20. A method of endarterectomy, comprising:

initiating a plane of separation between an atherosclerotic plaque and a layer of a vascular wall;

inserting an endarterectomy device having a flexible dissecting blade mounted on an elongated shaft into the plane of separation, the flexible dissecting blade having differential stiffness allowing the flexible dissecting blade to conform to an internal curvature of the vascular wall; and advancing the flexible dissecting blade of the endarterectomy device to longitudinally extend the plane of separation;

inserting a second endarterectomy device having a second flexible dissecting blade mounted on a second elongated shaft into the plane of separation; and advancing the second flexible dissecting blade of the second endarterectomy device to laterally extend the plane of separation.

21. A method of endarterectomy, comprising:

initiating a plane of separation between an atherosclerotic plaque and a layer of a vascular wall;

inserting an endarterectomy device having a flexible dissecting blade mounted on an elongated shaft into the plane of separation, the flexible dissecting blade having differential stiffness allowing the flexible dissecting blade to conform to an internal curvature of the vascular wall; and advancing the flexible dissecting blade of the endarterectomy device to longitudinally extend the plane of separation;

inserting a second endarterectomy device having a second flexible dissecting blade mounted on a second elongated shaft coaxially over the elongated shaft of the endarterectomy device into the plane of separation; and advancing the second flexible dissecting blade of the second endarterectomy device to laterally extend the plane of separation.

22. The method of claim 20, further comprising:

terminating the plane of separation between the atherosclerotic plaque and the layer of the vascular wall; and removing the atherosclerotic plaque.

23. The method of claim 21, further comprising:

terminating the plane of separation between the atherosclerotic plaque and the layer of the vascular wall; and removing the atherosclerotic plaque.

24. The endarterectomy device of claim 1, wherein said flexible dissecting blade is made of a flexible polymer or elastomer.

* * * * *